US012752132B2

(12) United States Patent
Yuds et al.

(10) Patent No.: US 12,752,132 B2
(45) Date of Patent: Oct. 6, 2026

(54) DEVICES AND TECHNIQUES FOR ULTRASOUND THERAPY VIA A DIALYSIS SYSTEM

(71) Applicant: Fresenius Medical Care Holdings, Inc., Waltham, MA (US)

(72) Inventors: David Yuds, Walnut Creek, CA (US); Martin Crnkovich, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 38 days.

(21) Appl. No.: 18/380,295

(22) Filed: Oct. 16, 2023

(65) Prior Publication Data

US 2025/0121213 A1 Apr. 17, 2025

(51) Int. Cl.
*A61N 7/00* (2006.01)

(52) U.S. Cl.
CPC ........ *A61N 7/00* (2013.01); *A61N 2007/0043* (2013.01)

(58) Field of Classification Search
CPC .......................... A61N 7/00; A61N 2007/0043
See application file for complete search history.

(56) References Cited

U.S. PATENT DOCUMENTS 10,974,079 B2 4/2021 Puleo
11,318,330 B2 5/2022 Puleo
2003/0092667 A1* 5/2003 Tachibana .......... A61K 41/0047 604/20
2016/0067398 A1 3/2016 Koch
2017/0042521 A1 2/2017 Popovic
2017/0157431 A1* 6/2017 Cheatham, III ... A61N 1/36021
2020/0188696 A1* 6/2020 Rousso .................... A61N 7/00
2020/0346043 A1 11/2020 Puleo
(Continued)

FOREIGN PATENT DOCUMENTS

CN 108144147 A 6/2018
CN 209476168 U 10/2019
(Continued)

OTHER PUBLICATIONS

International Search Report and Written Opinion for International Application No. PCT/US2024/045489, mailed on Dec. 3, 2024, 20 pages.
(Continued)

*Primary Examiner* — Alexei Bykhovski
(74) *Attorney, Agent, or Firm* — KDW Firm PLLC

(57) ABSTRACT

A dialysis-ultrasound system is described that includes an ultrasound therapy device integrated with a catheter to incorporate ultrasound therapy into a dialysis system. The ultrasound device may be or may include a high-intensity focused ultrasound (HIFU) device or peripheral focused ultrasound stimulation (pFUS) device. The ultrasound therapy may target the liver, for example, to treat diabetes. In one example, a system includes a catheter configured to be arranged within the peritoneal cavity of a patient for peritoneal dialysis (PD), and an ultrasound device configured to emit ultrasound waves. The ultrasound device is integrated with the catheter and is arranged on the catheter to be implanted within the peritoneal cavity of the patient to provide ultrasound therapy to a target region of the patient. Other embodiments are described.

20 Claims, 7 Drawing Sheets

(56) References Cited

U.S. PATENT DOCUMENTS

| | | | | |
|---|---|---|---|---|
| 2020/0406065 | A1 * | 12/2020 | Puleo | A61N 1/36034 |
| 2020/0406066 | A1 | 12/2020 | Puleo | |
| 2021/0015454 | A1 | 1/2021 | Puleo | |
| 2022/0047793 | A1 * | 2/2022 | Manda | A61M 25/0068 |
| 2022/0175306 | A1 * | 6/2022 | Cotero | A61B 5/4848 |
| 2023/0008094 | A1 * | 1/2023 | Roy | A61M 1/287 |

FOREIGN PATENT DOCUMENTS

| | | | |
|---|---|---|---|
| UA | 86519 | U | 1/2014 |
| WO | 2016090175 | A1 | 6/2016 |
| WO | 2020102652 | A1 | 5/2020 |
| WO | 20210207161 | A1 | 10/2021 |
| WO | WO-2023004346 | A1 * | 1/2023 |

OTHER PUBLICATIONS

Yuntao Lu, “Recent advances in power supply strategies for untethered neural implants,” Journal of Micromechanics and Microengineering, vol. 31, No. 10, Sep. 1, 2021, p. 104003, XP020369243.

Cotero et al., “Focused Ultrasound Modulation of Hepatic Neural Plexus Restores Glucose Homeostasis in Diabetes” bioRxiv—doi: https://doi.org/10.1101/2021.04.16.440207—posted Apr. 18, 2021.

* cited by examiner

DEVICES AND TECHNIQUES FOR ULTRASOUND THERAPY VIA A DIALYSIS SYSTEM

FIELD

The disclosure generally relates to devices and processes for internal ultrasound therapy of one or more patient organs to treat a condition, for example, ultrasound stimulation of a portion of the liver to treat diabetes, and, more particularly, to incorporating an ultrasound therapy device with a peritoneal dialysis (PD) system to facilitate ultrasound therapy within an existing dialysis treatment regimen for a patient.

BACKGROUND

Renal dysfunction or failure, for example, end-stage renal disease (ESRD), causes the body to lose the ability to remove water and minerals and excrete harmful metabolites, maintain acid-base balance, and control electrolyte and mineral concentrations within physiological ranges. Toxic uremic waste metabolites including urea, creatinine, and uric acid accumulate in the body's tissues which can result in adverse health effects if the filtration function of the kidney is not replaced. Dialysis is the typical treatment used to replace kidney function by removing these waste toxins and excess water.

Peritoneal dialysis (PD) is one of two common dialysis treatments (hemodialysis (HD) being the other prominent type). In PD, a dialysis solution is run through a tube (i.e., a catheter) into the peritoneal cavity, the abdominal body cavity around the intestine. The peritoneal membrane acts as a membrane for removing waste and excess water from the blood. The therapy involves cycles of dialysis fluid inflow, fluid dwell, and dialysis fluid outflow. Automatic PD systems (or cyclers) can run a series of cycles to implement a full treatment for a patient. PD can be carried out at a patient's home (for instance, overnight via an automatic PD system), which frees patients from the routine of having to go to a dialysis clinic on a fixed schedule multiple times per week and reduces resources, such as trained clinicians, from having to perform the dialysis process for the patient.

Dialysis patients typically have certain health conditions at higher rates than the general population. For example, the incidence rate of dialysis is much greater in persons with diabetes compared with individuals without diabetes. Diabetes makes it difficult for the pancreas (located within the peritoneal cavity) to regulate glucose (sugar) levels in the body, therefore, diabetes becomes a co-morbidity for dialysis patients who have both conditions.

Accordingly, dialysis patients typically require therapy for other conditions in addition to dialysis treatment. These individual treatments require separate treatment devices, medications, healthcare facility visits, and/or resources, such as doctors and/or other healthcare providers to administer each treatment. Multiple treatment regimens for different conditions increases resource costs (financial, time, etc.), causes a burden for patients, and makes it difficult for patients to adhere to each protocol, reducing the probability of a successful outcome for each health issue.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one example, a system may include a catheter configured to be arranged within the peritoneal cavity of a patient for peritoneal dialysis (PD), and an ultrasound device configured to emit ultrasound waves, the ultrasound device integrated with the catheter and arranged on the catheter to be implanted within the peritoneal cavity of the patient to provide ultrasound therapy to a target region of the patient.

In some examples of the system, the ultrasound device may include one of a high-intensity focused ultrasound (HIFU) device or peripheral focused ultrasound stimulation (pFUS) or device.

In various examples of the system, the target region may include a portion of at least one of the liver, the pancreas, or the intestines.

In some examples of the system, the ultrasound device may include a power unit configured to be wirelessly charged via a wireless power source.

In exemplary examples of the system, the power unit may be operative via electrodynamic wireless power transfer (EWPT).

In some examples of the system, the power unit may be operative via one or more of a triboelectric effect, photonic power transfer, or kinetic charging.

In various examples of the system, the system may further include a patient sensor configured to measure a patient factor, and a dialysis machine fluidically coupled to the catheter and configured to perform PD on the patient, at least one PD parameter of the PD determined based on the patient factor.

In some examples of the system, the patient sensor may include a blood glucose sensor.

In exemplary examples of the system, the PD parameter may include a dialysate concentration.

In some examples of the system, the patient sensor may include a pressure sensor configured to measure an intraperitoneal pressure.

In some examples of the system, the ultrasound therapy may be configured to treat diabetes.

In one example, a method may include implanting an ultrasound device configured to emit ultrasound waves within the peritoneal cavity of a patient via a peritoneal dialysis (PD) catheter implantation procedure, wherein the ultrasound device is integrated with the catheter and arranged on the catheter in a position to provide ultrasound therapy to a target region of the patient when implanted in the peritoneal cavity, and performing ultrasound therapy by causing the ultrasound device to emit the ultrasound waves incident on the target region.

In some examples of the method, the ultrasound device may include one of a high-intensity focused ultrasound (HIFU) device or peripheral focused ultrasound stimulation (pFUS) or device.

In various examples of the method, the target region may include a portion of at least one of the liver, the pancreas, or the intestines.

In some examples of the method, the ultrasound device may include a power unit configured to be wirelessly charged via a wireless power source.

In various examples of the method, the power unit may be operative via electrodynamic wireless power transfer (EWPT).

In some examples of the method, the power unit may be operative via one or more of a triboelectric effect, photonic power transfer, or kinetic charging.

In exemplary examples of the method, further comprising receiving a measurement of a patient factor determined via a patient sensor, and performing PD on the patient using at least one PD parameter determined based on the patient factor.

In some examples of the method, the patient sensor may include a blood glucose sensor.

In various examples of the method, the PD parameter may include a dialysate concentration.

In some examples of the method, the patient sensor may include a pressure sensor configured to measure an intraperitoneal pressure.

In some examples of the method, the ultrasound therapy may be configured to treat diabetes.

BRIEF DESCRIPTION OF THE DRAWINGS

By way of example, specific embodiments will now be described, with reference to the accompanying drawings, in which.

DETAILED DESCRIPTION

Figure 1A:
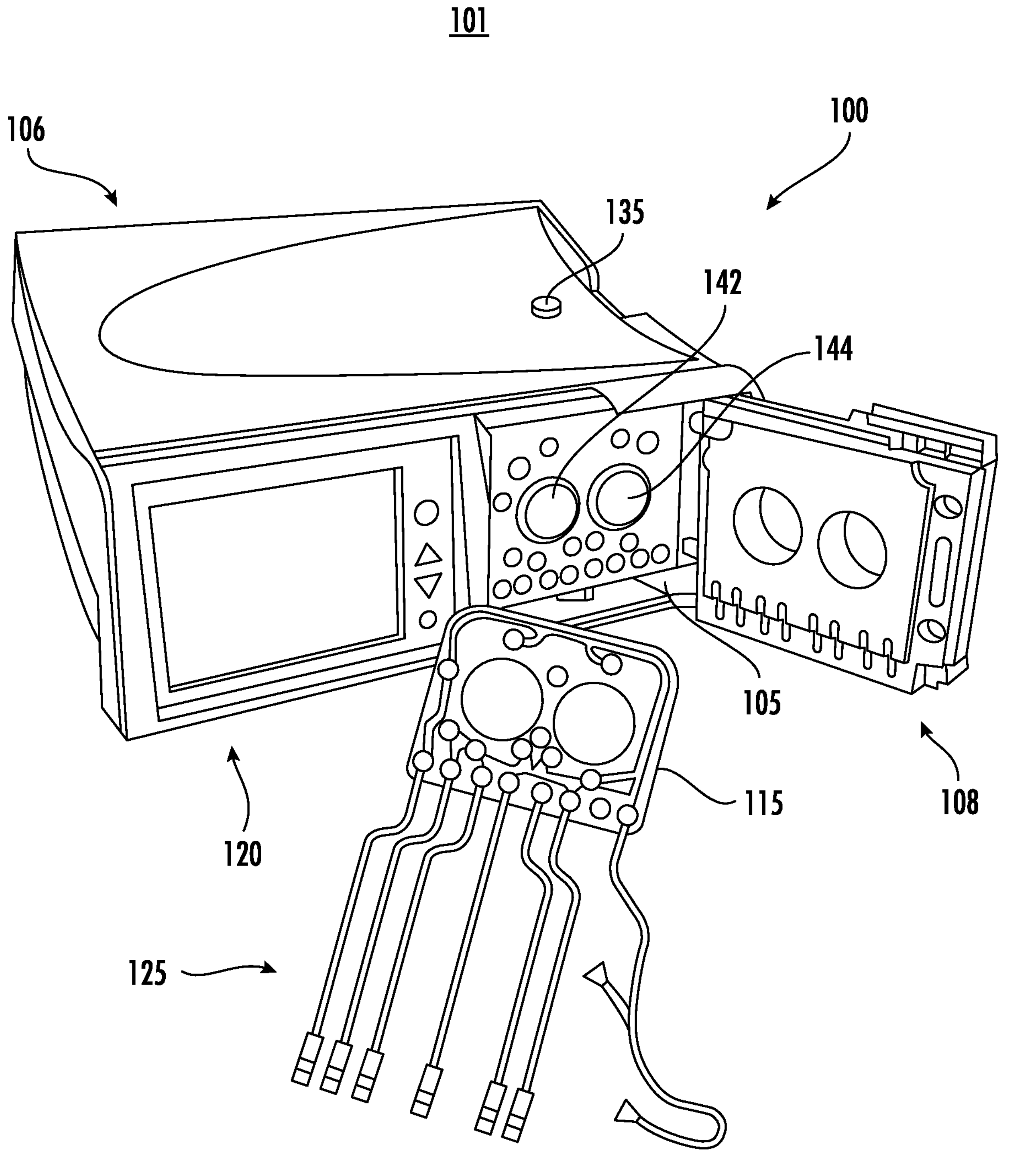
FIGS. 1A and 1B illustrate an exemplary PD system in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Various features of an improved dialysis system incorporating ultrasound therapy (a "dialysis-ultrasound system") will now be described more fully hereinafter with reference to the accompanying drawings, in which one or more features of the dialysis-ultrasound system will be shown and described. It should be appreciated that the various features may be used independently of, or in combination, with each other. It will be appreciated that a dialysis-ultrasound system as disclosed herein may be embodied in many different forms and should not be construed as being limited to the examples set forth herein. Rather, these examples are provided so that this disclosure will convey certain features of the dialysis-ultrasound system to those skilled in the art.

The present disclosure describes a dialysis-ultrasound system that includes an ultrasound (or ultrasonic) device integrated with one or more portions of a dialysis system. In some embodiments, the dialysis system may be or may include a peritoneal dialysis (PD) system. In various embodiments, the ultrasound device may be integrated with, coupled to, or otherwise associated with a catheter of the PD dialysis system, for instance, a portion of the catheter inserted into the patient for use during a PD treatment. In some embodiments, the ultrasound device may be or may include a high-intensity focused ultrasound (HIFU) device or peripheral focused ultrasound stimulation (pFUS) system or device. In various embodiments, the ultrasound device may be configured, and may be arranged within a patient in conjunction with the catheter, to provide ultrasound waves, energy, signals, etc. incident on a target region to treat diabetes. For example, the ultrasound device may operate to provide selective activation of the nerve plexus of the hepatic portal system via peripheral focused ultrasound stimulation (pFUS) to improve glucose homeostasis. In this manner, a dialysis-ultrasound system may operate to provide dialysis treatment while concurrently treating diabetes.

Figure 1B:
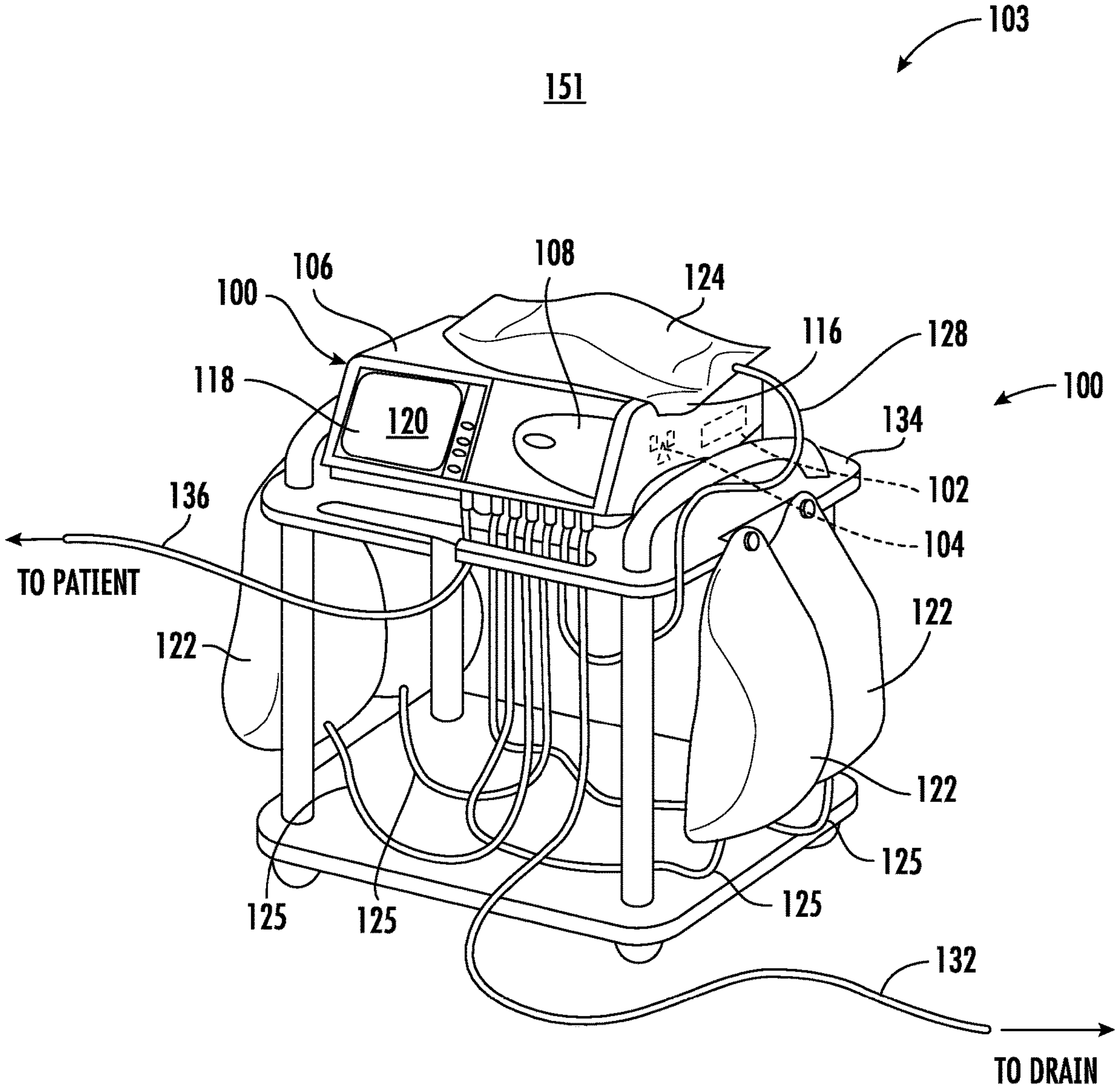
Figure 2:
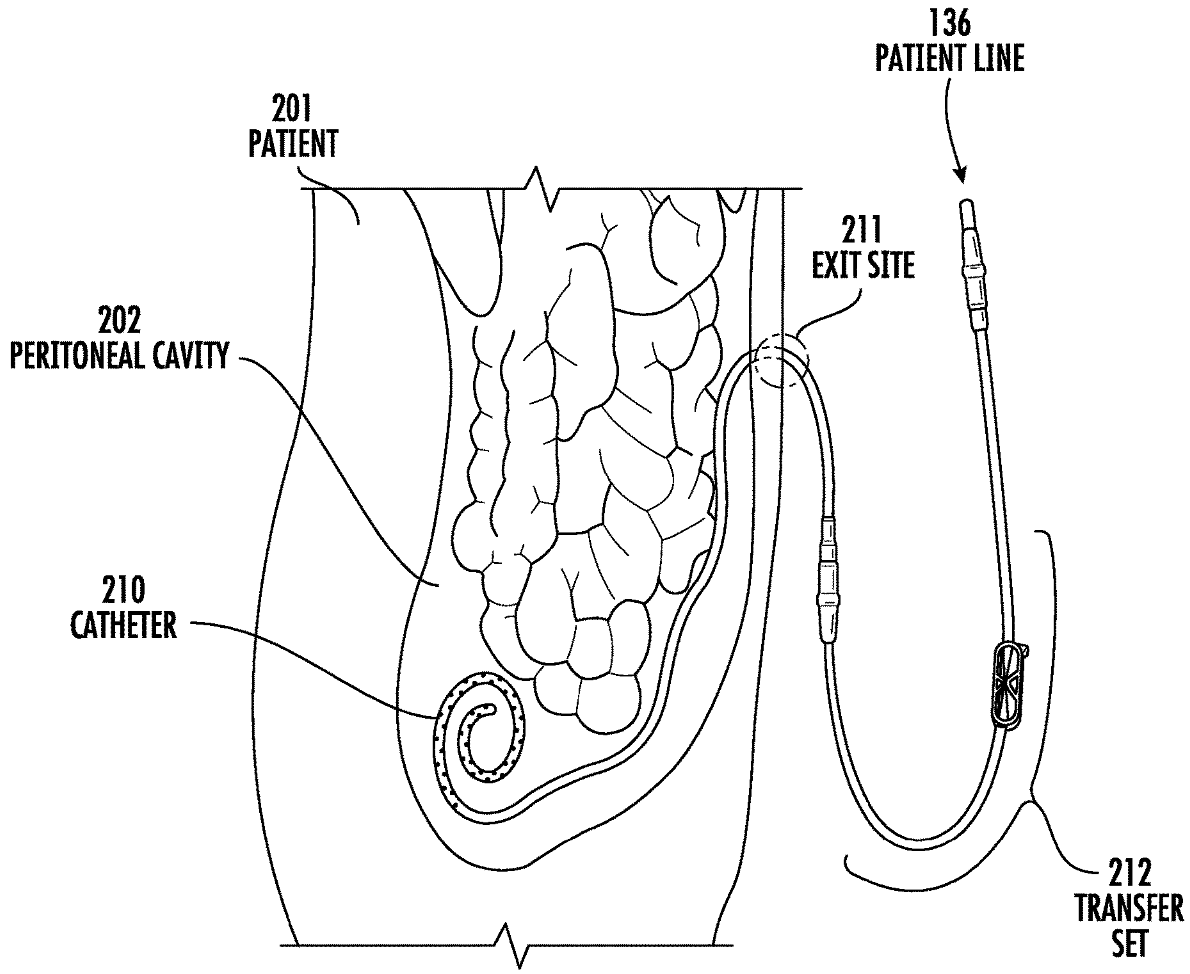
FIG. 2 illustrates an exemplary PD catheter implanted within a patient in accordance with the present disclosure.

PD patients receive dialysis therapy in the course of filling, dwelling, and draining dialysate solution via a catheter (see, for example, FIGS. 1A, 1B, and 2). The dialysate solution is a liquid drug that is comprised of various salts, minerals, and sugars like dextrose or lactose. The PD catheter is implanted by a surgeon. The catheter's tubing is made from soft, flexible polyurethane or silicone and is anchored into the wall of the patient's belly or chest with a cuff (e.g., a Dacron cuff) at the exit site. A dialysis system connects to the end of this tubing outside of the exit site. The tip of the catheter in the base of the peritoneal cavity may be coiled or straight and features multiple holes where the dialysate solution flows in and out of the patient's peritoneal cavity during treatment. Illustrative PD systems include an ambulatory PD (APD) system and a continuous APD (CAPD) system.

Dialysis patients have a higher incidence rate of diabetes compared with the general population. For example, the average annual incidence rate of dialysis can be as much as twelve times greater in persons with diabetes, and diabetic patients comprise over half of the incident dialysis population. The average annual prevalence rate of kidney failure can be as much as ten times greater for diabetic patients. In addition, patients with diabetes typically have more comorbidities at the start of dialysis and poorer survival rates.

Because diabetes makes it difficult for the patient's pancreas (also located within the peritoneum) to regulate glucose (sugar) levels in the body, diabetes is a co-morbidity for dialysis patients who have both conditions. It is challenging for physicians to manage the patient's therapy when the sugar (dextrose or lactose) from the dialysate solution cannot be regulated by the patient's pancreas, ultimately leading to patients taking more costly medications where compliance is essential; there can be no deviations in the many pills a patient must take each day.

Focused ultrasound has the potential to provide benefits for diabetic patients. For example, focused ultrasound may improve or even fully restore glucose homoeostasis, while reducing (or potentially even eliminating) the number and/or dosage of drugs required to regulate diabetes. Research has indicated that the selective targeting of the liver with ultrasound may improve diabetic complications. For example, studies have indicated that the selective activation at the nerve plexus of the hepatic portal system via peripheral focused ultrasound stimulation (pFUS) may improve glucose homoeostasis. See, for example, Cotero et al., "Stimulation of the hepatoportal nerve plexus with focused ultrasound restores glucose homoeostasis in diabetic mice, rats and swine," Nat. Biomed. Eng 6, 683-705 (2022) (the "Cotero Study"), the contents of which are hereby incorporated by reference into the present disclosure.

The Cotero Study involved non-invasive ultrasound targeting techniques. The Cotero Study indicated that pFUS modulated the activity of sensory projections to the hypothalamus, altered the concentrations of metabolism-regulating neurotransmitters, and enhanced glucose tolerance and utilization, however, physical transection or chemical blocking of the liver-brain nerve pathway abolished the effect of pFUS on glucose tolerance. The Cotero Study also indicated that longitudinal multi-omic profiling of metabolic tissues suggested that pFUS induced modifications of key metabolic functions in the liver, pancreas, muscle, adipose, kidney and intestinal tissues. For example, approximately three-minutes of focused ultrasound on the liver per day could be enough to cause the body to regulate (or better regulate) blood glucose levels. Accordingly, ultrasound activation of afferent autonomic nerves may represent a non-pharmacologic therapy for the restoration of glucose homoeostasis in diabetes, for instance, type-2 diabetes, and other metabolic diseases.

As indicated in the Cotero study, ultrasound therapy could be administered non-invasively, however, current ultrasound tools used to perform this kind of pFUS technique require trained technicians. Even with the prevalence of diabetes among dialysis patients who visit a dialysis clinic three times a week for in-center dialysis, it is impractical and cost-prohibitive to hire thousands of ultrasound technicians to treat patients, which would still not be sufficient to meet the three-minutes per day target.

Sustained ultrasound therapy may be a valuable treatment for diabetes over the duration of a patient's life. Ultrasound technology exists to simplify and automate these systems in a way that could be used by patients at home. However, existing systems are not capable of providing ultrasound-based diabetes treatment that can be widely deployed.

A large segment of the population of dialysis patients also has diabetes, which are co-morbidities that affect each other. Managing diabetes and dialysis using existing techniques requires separate treatment regimens, each with their own set of medications, equipment, healthcare providers, and time obligations for attending to the various requirements. The health effects of diabetes and dialysis lead to complications in treatment for both conditions, with diabetes mainly being addressed using costly medication that is strongly dependent upon patient compliance.

PD patients already require a catheter to be inserted into their peritoneal cavity. Accordingly, incorporating an ultrasound device with the catheter allows for an invasive approach that does not require a separate procedure for inserting the ultrasound device as the ultrasound-catheter (e.g., an ultrasound device integrated with a catheter according to some embodiments) can be inserted into the patient during the catheter insertion procedure for PD dialysis. Since the PD catheter required for dialysis is implanted and can be reliably routed past the liver (or within range of the liver by an ultrasound device), a dialysis-ultrasound system according to some embodiments provides technological advantages over existing systems by integrating an ultrasound device as part of an implanted PD catheter. By incorporating an ultrasound device with the PD catheter and, for example, powering it wirelessly, diabetic patients can forego medications and tolerate higher dialysate solution concentrations for improved ultrafiltration. The combined ultrasound-dialysis treatment can lead to significant improvements in health outcomes and cost savings from reduced diabetes medication needs.

FIGS. 1A and 1B show an example of a peritoneal dialysis (PD) system 101, which is configured in accordance with an exemplary embodiment of the system described herein. In some implementations, the PD system 101 may be a home PD system, e.g., a PD system configured for use at a patient's home. The dialysis system 101 may include a dialysis machine 100 (e.g., a peritoneal dialysis machine 100, also referred to as a PD cycler) and in some embodiments the machine may be seated on a cart 134.

The dialysis machine 100 may include a housing 106, a door 108, and a cartridge interface including pump heads 142, 144 for contact with a disposable cassette, or cartridge 115, where the cartridge 115 is located within a compartment formed between the cartridge interface and the closed door 108 (e.g., cavity 105). Fluid lines 125 may be coupled to the cartridge 115 in a known manner, such as via a connector, and may further include valves for controlling fluid flow to and from fluid bags, including fresh dialysate and warming fluid. In another embodiment, at least a portion of the fluid lines 125 may be integral to the cartridge 115. Prior to operation, a user may open the door 108 to insert a fresh cartridge 115 and to remove the used cartridge 115 after operation.

The cartridge 115 may be placed in the cavity 105 of the machine 100 for operation. During operation, dialysate fluid may flow into a patient's abdomen via the cartridge 115, and spent dialysate, waste, and/or excess fluid may be removed from the patient's abdomen via the cartridge 115. The door 108 may be securely closed to the machine 100. Peritoneal dialysis for a patient may include a total treatment of approximately 10 to 30 liters of fluid, where approximately 2 liters of dialysate fluid are pumped into a patient's abdomen, held for a period of time, e.g., about an hour (the dwell duration), and then pumped out of the patient. This is repeated until the full treatment volume is achieved, and may, for example, occur overnight while a patient sleeps.

A heater tray 116 may be positioned on top of the housing 106. The heater tray 116 may be any size and shape to accommodate a bag of dialysate (e.g., a 5-liter (L) bag of dialysate) for batch heating. The dialysis machine 100 may also include a user interface such as a touch screen 118 and control panel 120 operable by a user (e.g., a caregiver or a patient) to allow, for example, set up, initiation, and/or termination of a dialysis treatment. In some embodiments, the heater tray 116 may include a heating element 135 for heating the dialysate prior to delivery into the patient.

Dialysate bags 122 may be suspended from hooks on the sides of the cart 134, and a heater bag 124 may be positioned on the heater tray 116. Hanging the dialysate bags 122 may improve air management as air content may be disposed by gravity to a top portion of the dialysate bag 122. Although four dialysate bags 122 are illustrated in FIG. 1B, any number "n" of dialysate bags may be connectable to the dialysis machine 100 (e.g., 1 to 5 bags, or more), and reference made to first and second bags does not limit the total number of bags used in a dialysis system 101. For example, the dialysis machine may have dialysate bags 122*a*, . . . 122*n* connectable in the system 101. In some embodiments, connectors and tubing ports may connect the dialysate bags 122 and lines for transferring dialysate. Dialysate from the dialysate bags 122 may be transferred to the heater bag 124 in batches. For example, a batch of dialysate may be transferred from the dialysate bags 122 to the heater bag 124, where the dialysate is heated by the heating element 135. When the batch of dialysate has reached a predetermined temperature (e.g., approximately 98°-100° F., 37° C.), the batch of dialysate may be flowed into the patient. The dialysate bags 122 and the heater bag 124 may be connected to the cartridge 115 via dialysate bag lines or tubing 125 and a heater bag line or tubing 128, respectively. The dialysate bag lines 125 may be used to pass dialysate from dialysate bags 122 to the cartridge 115 during use, and the heater bag line 128 may be used to pass dialysate back and forth between the cartridge and the heater bag 124 during use. In addition, a patient line 136 and a drain line 132 may be connected to the cartridge 115. The patient line 136 may be connected to a patient's abdomen via a catheter and may be used to pass dialysate back and forth between the cartridge and the patient's peritoneal cavity by the pump heads 142, 144 during use. The drain line 132 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 125), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 118 and the control panel 120 may allow an operator to input various treatment parameters to the dialysis machine 100 and to otherwise control the dialysis machine 100. In addition, the touch screen 118 may serve as a display. The touch screen 118 may function to provide information to the patient and the operator of the dialysis system 101. For example, the touch screen 118 may display information related to a dialysis treatment to be applied to the patient, including information related to a prescription.

The dialysis machine 100 may include a processing module 102 that resides inside the dialysis machine 100, the processing module 102 being configured to communicate with the touch screen 118 and the control panel 120. The processing module 102 may be configured to receive data from the touch screen 118 the control panel 120 and sensors, e.g., weight, air, flow, temperature, and/or pressure sensors, and control the dialysis machine 100 based on the received data. For example, the processing module 102 may adjust the operating parameters of the dialysis machine 100.

The dialysis machine 100 may be configured to connect to a network 103. The connection to network 103 may be via a wired and/or wireless connection. The dialysis machine 100 may include a connection component 104 configured to facilitate the connection to the network 103. The connection component 104 may be a transceiver for wireless connections and/or other signal processor for processing signals transmitted and received over a wired connection. Other medical devices (e.g., other dialysis machines) or components may be configured to connect to the network 103 and communicate with the dialysis machine 100.

The user interface portion such as the touch screen 118 and/or control panel 120 may include one or more buttons for selecting and/or entering user information. The touch screen 118 and/or control panel 120 may be operatively connected to a controller (not shown) and disposed in the machine 100 for receiving and processing the inputs to operate the dialysis machine 100.

Dialysis system 101 depicted in FIGS. 1A and 1B may be the same or similar to the Liberty® Cycler produced by Fresenius Medical Care North America of Waltham, Massachusetts, United States of America. However, embodiments are not so limited, as FIGS. 1A and 1B depict an illustrative dialysis system according to one example. Embodiments may include, use, or be used in combination with various types of dialysis systems currently known to persons of skill in the art or developed in the future, including PD systems.

FIG. 2 illustrate an exemplary PD catheter implanted within a patient in accordance with the present disclosure. As shown in FIG. 2, a catheter 210 may be inserted into the peritoneal cavity 202 of a patient 201. The catheter 210 may be coupled to a transfer set 212 fluidically coupled to the patient line 136 and, ultimately, to the dialysis system 101 for performing PD on the patient 201.

The catheter 210 may exit the patient 201 at an exit site 211. The exit site 211 may be arranged in various locations depending on certain factors, such as patient anatomy, healthcare professional preference, and/or the like. The exit site 211 may be a lateral/medial distance and an inferior/superior distance with respect to the umbilicus. For example, the exit site 211 may be lateral with respect to the umbilicus by about 6 inches, about 5 inches, about 4 inches, about 3 inches, about 2 inches, about 1 inch, about 0.5 inches, and/or any value or range between any two of these values (including endpoints). In another example, the exit site 211 may be inferior (or superior) with respect to the umbilicus by about 6 inches, about 5 inches, about 4 inches, about 3 inches, about 2 inches, about 1 inch, about 0.5 inches, and/or any value or range between any two of these values (including endpoints).

Figure 3:
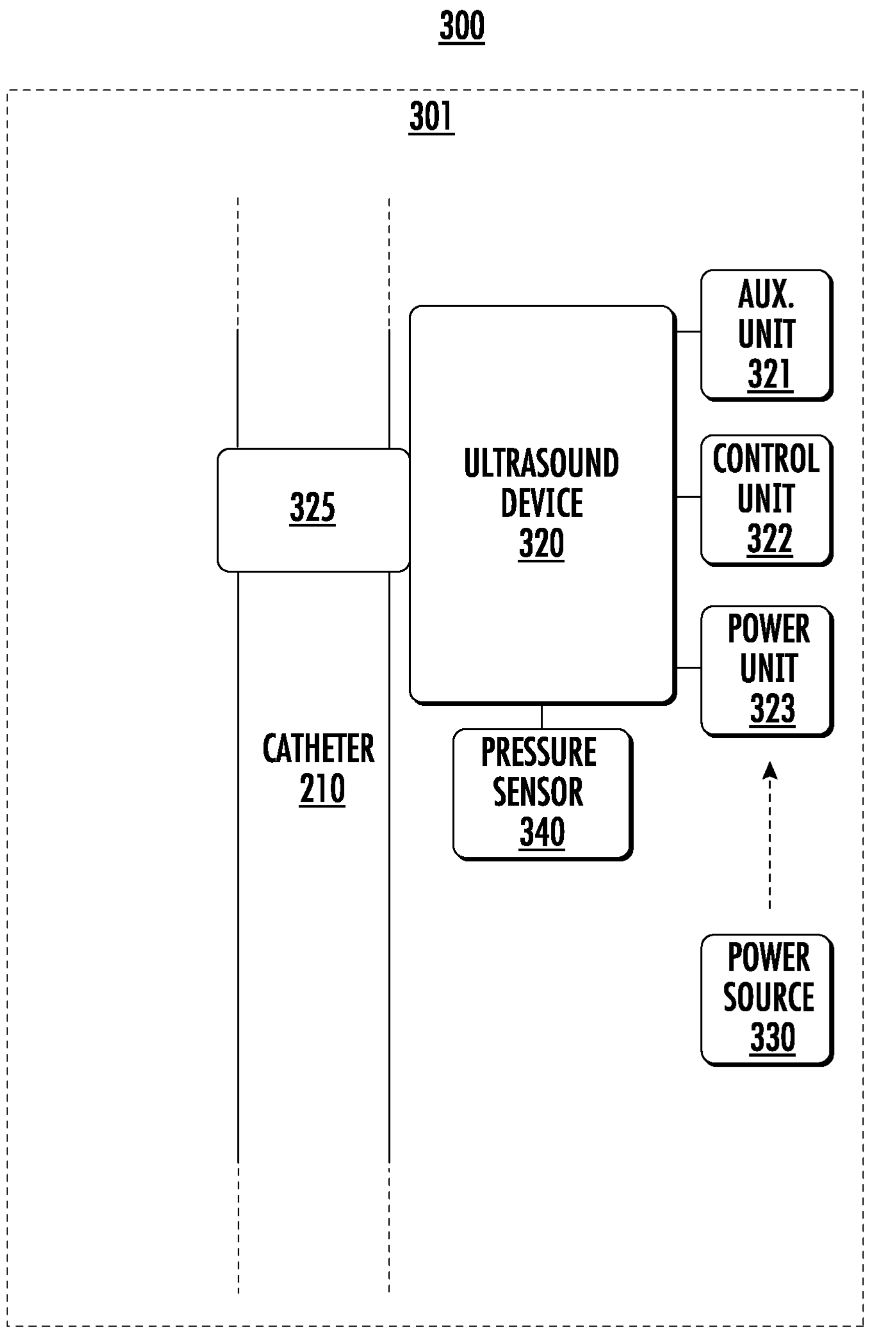
FIG. 3 illustrates an exemplary catheter-ultrasound system in accordance with the present disclosure.

FIG. 3 illustrates an exemplary catheter-ultrasound system in accordance with the present disclosure. As shown in FIG. 3, a catheter-ultrasound system 301 may include an ultrasound device 320 integrated with a catheter 210. In some embodiments, the ultrasound device 320 may be coupled to the catheter 210 via a coupling element 325. Non-limiting examples of the coupling element 325 may include a clip, a clasp, a friction fit element, a clamp, a fastener, and/or the like. In various embodiments, a coupling element 325 may not be required. For example, the ultrasound device 320 may be formed, shaped, or otherwise arranged to be integrated with the catheter 210. For instance, the ultrasound device 320 may include a hollow portion configured to receive the catheter 210 (e.g., the catheter 210 can pass through the hollow portion; the ultrasound device 320 is coupled to the catheter within the hollow portion). In some embodiments, the ultrasound device 320 may be affixed to the catheter 210 via an adhesive. In various embodiments, the catheter 210 may be formed with a coupling element (not shown) configured to mount, affix, or otherwise couple an ultrasound device 320 to the catheter 210. The catheter coupling element may be or may include a flange, projections, grooves, clips, clamps, and/or the like.

In various embodiments, the location of the ultrasound device 320 along the catheter 210 (for instance, a distance from an end of the catheter) may be determined so that the ultrasound device 320 is positioned within a predetermined region of the peritoneal cavity 202 of the patient, for example, to be incident on a target region (with sufficient ultrasound frequency).

The ultrasound device 320 may be configured to emit sound waves at various frequencies. In various embodiments, the ultrasound device may be configured to operate at a frequency of about 50 kHz to about 10 MHz. In some embodiments, the ultrasound device may be configured to operate at a frequency of about 100 kHz to about 1 MHz. A non-limiting example frequency is about 1 Hz, about 5 Hz, about 10 Hz, about 50 Hz, about 100 Hz, about 500 Hz, about 1 MHz, about 2 MHz, about 5 MHz, about 10 MHz, about 100 MHz, about 500 MHz, about 1 kHz, about 5 kHz, about 10 kHz, about 100 kHz, and/or any value or range between any two of these values (including endpoints).

In some embodiments, the ultrasound device 320 may be configured to emit ultrasound energy at various pulses or bursts (e.g., durations of activation). Non-limiting examples of bursts may include every 1 second, every 2 seconds, every 3 seconds, every 4 seconds, every 5 seconds, every 6 seconds, every 7 seconds, every 8 seconds, every 9 seconds, every 10 seconds, every 15 seconds, every 20 seconds, every 30 seconds, and/or any value or range between any two of these values (including endpoints). In some embodiments, the bursts may be about every 1 to 10 about seconds. In various embodiments, the bursts may be about every 1 to about 5 seconds.

The ultrasound device 320 may include various types of ultrasound-emitting devices, elements, and/or the like. In various embodiments, the ultrasound device 320 may be or may include an ultrasound transducer. In some embodiments, the ultrasound device 320 may be or may include a HIFU device, a pFUS device, and/or the like. Non-limiting examples of ultrasound-emitting devices are ultrasound transducers provided by Sonic Concepts of Bothell, Washington, United States of America, including, without limitation, the H-Transducer Series (e.g., H-106).

In some embodiments, the ultrasound device 320 may include or may be operably coupled to one or more auxiliary devices 321 configured to facilitate the operation of the ultrasound device 320. Non-limiting examples of the auxiliary devices 321 may include amplifiers, radio frequency (RF) amplifiers, a network (e.g., an RF impedance matching network to sustain the efficiency and bandwidth of the ultrasound device 320), and/or the like. In exemplary embodiments, one or more of the auxiliary devices 321 may be integrated into or within the ultrasound device 320.

In various embodiments, the ultrasound device 320 may include or may be operably coupled to a control unit 322. In some embodiments, the control unit 322 may include hardware, software, circuitry, and/or the like configured to control the operations of the ultrasound device 320. For example, the control unit 322 may include software and/or hardware (see, for example, FIG. 5) configured to control the operating frequency, signal duration, signal burst period (e.g., time between bursts), burst duration, and/or the like of the ultrasound device 320. In exemplary embodiments, the control unit 322 may be wirelessly coupled to an external computing device for control, communications, status, and/or the like by the patient, healthcare professional, or other operator. In exemplary embodiments, the control unit 322 may be integrated into or within the ultrasound device 320.

In exemplary embodiments, the ultrasound device 320 may include or may be operably coupled to a power unit 323. In some embodiments, the power unit 323 may be operative to provide power to the ultrasound device 320, the control unit 322, and/or any auxiliary units 321. In various embodiments, the power unit 323 may be or may include a battery, including, for example, a rechargeable battery. In some embodiments, the power unit 323 may be configured to be charged wirelessly, for instance, via a remote power source. In various embodiments, the power unit 323 may operate as a wireless power transfer (WPT) system configured to receive wireless power signals, energy, and/or the like from the power source 330.

For example, in one embodiment, the power unit 323 may be or may include an electrodynamic wireless power transfer (EWPT) system configured to utilize a receiver (e.g., located within the power unit 323) with a mechanically resonating or rotating permanent magnet. When subjected to a time-varying magnetic field, the mechanical motion of the resonating magnet is converted into electricity by one or more electromechanical transduction schemes (e.g. electromagnetic/induction, piezoelectric, or capacitive). An EWPT system leverages low-frequency magnetic fields (<1 kHz), which safely pass through conductive media and have higher human field exposure limits (~2 mTrms at 1 kHz), which are safe for biomedical environments.

In a EWPT embodiment, a receiver with a mechanically resonating or rotating magnet may be arranged inside the ultrasound device 320 (e.g., a receiver of the power unit 323) and powered when the patient or other operator positions a complementary magnetic field generator (e.g., a power source 330) that produces low-frequency magnetic fields incident on the receiver. In various embodiments, the magnetic field generator may take the form of or may be incorporated into a battery-powered belt, a chair or mat, the dialysis machine itself, and/or the like. The magnetic field generator may contain a chipset or other control unit to control the power (magnetic field) delivery and, in some examples, a foreign object detection technology to make sure that other objects that are not paired with the charger do not inadvertently receive a charge.

In another example, in some embodiments, the power unit 322 may be charged via the triboelectric effect, in which certain materials become electrically charged when they are rubbed against one another. For instance, externally applied ultrasound waves or other wireless energy (for instance, from the power source 330) may be incident on the power unit 322 to cause thin layers of triboelectric, ferroelectric, and/or the like materials to vibrate back and forth between two electrode layers, resulting in the generation of an electrical current for operating the ultrasound device 320, charging a battery of the power unit 322, and/or the like. In various embodiments, a hydrogel may be subjected to the ultrasound waves or other wireless energy to cause the triboelectric effect within the power unit 322.

In additional or alternative examples, in some embodiments, biocompatible charging processes may include light (photonic power transfer), heartbeats, and kinetic energy, for instance, via body movements. For example, for the photonic power transfer, a light source may be attached to or otherwise be incident on the patient (for instance, a patch of micro-LEDs) that shines light through the patient tissue to a corresponding photovoltaic device electrically coupled to the power unit 322. For the heartbeat-based system, the movement of the beating of the heart may be transferred to provide kinetic energy-based charging, for instance, winding a mechanical spring that, once fully wound, can unwind to power a micro-generator inside the heartbeat-based system. The micro-generator can be electrically coupled to the power unit 322 to power the ultrasound device 320 and/or to recharge a battery. For the kinetic energy-based system, a flexible piezoelectric nanogenerator may be used to generate energy using electrical energy produced from body movements of the patient. Embodiments are not limited in this context.

In some embodiments, the catheter-ultrasound system 301 may include one or more sensors for determining patient information, such as temperatures, pressures, and/or the like. In various embodiments, the one or more sensors may be powered via the power unit 323 and/or the power source 330. In exemplary embodiments, a portion of the power from power unit 323 may be used to power a sensor. In other embodiments, the sensor may include a power unit (e.g., battery, charged via power source 330, and/or the like).

In one example, according to various embodiments, the catheter-ultrasound system 301 may include a pressure sensor 340. In some embodiments, the pressure sensor 340 may be a part of, integral with, coupled to, or otherwise associated with the ultrasound device 320. In other embodiments, the pressure sensor 340 may not be a part of the ultrasound device 320, for instance, and may be coupled to the catheter 320. In some embodiments, due to the location of the pressure sensor 340 within the peritoneal cavity, the pressure sensor 340 may be configured to monitor the intraperitoneal pressure. For example, The pressure sensor 340 may be configured to provide pressure monitoring to reduce or even eliminate overfill situations and determine the efficacy of the dwell portion of the cycle (e.g., as the glucose concentration pulls fluid from the rest of the body, the intraperitoneal pressure increases until the body begins to equilibrate and give back the fluid, at which point a PD machine may drain the fluid and begin a new cycle for maximum efficiency). In some embodiments, pressure readings from the pressure sensor 340 may be used to control a PD machine, for instance, initiating drain cycles, starting a new cycle, and/or the like based on conditions within the peritoneal cavity indicated by the pressure readings.

Figure 4:
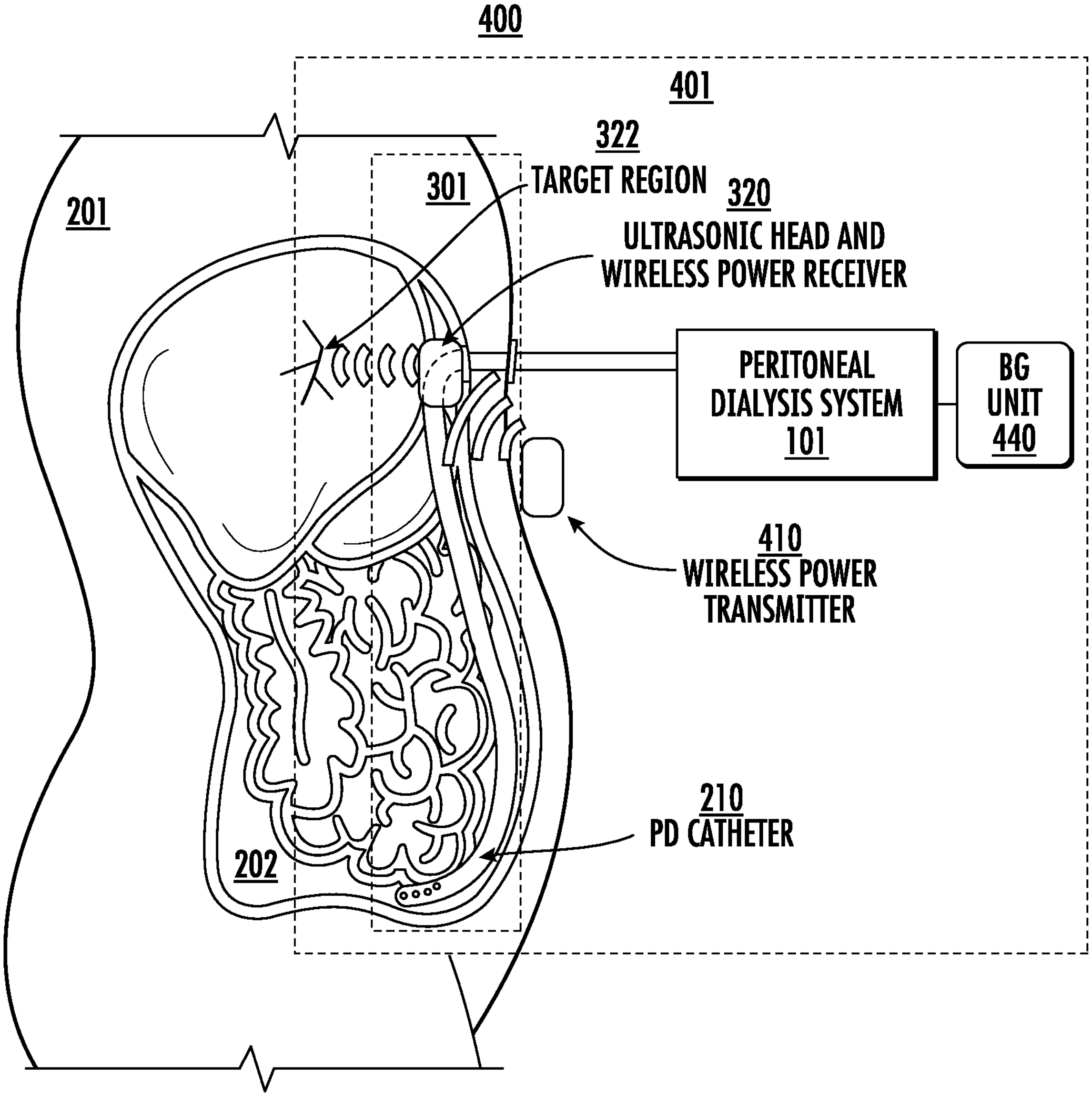
FIG. 4 illustrates a first exemplary operating environment in accordance with the present disclosure.

FIG. 4 illustrates an exemplary operating environment in accordance with the present disclosure. As shown in FIG. 4, operating environment 400 may include a dialysis-ultrasound system 401 that includes a catheter-ultrasound system 301 and a PD dialysis system 101. The catheter-ultrasound system 301 includes a catheter 201 coupled to an ultrasound device 320. The catheter 202 may be arranged within the peritoneal cavity 202 of the patient 201. The catheter 210 may be fluidically coupled to a PD system 101 for providing PD therapy to the patient 201.

The catheter 210 may be implanted within the patient 201 such that the ultrasound device 320 is also arranged within the patient, for instance, within the peritoneal cavity 202. The ultrasound device 320 may be arranged within the patient 201 at an implant location so that the ultrasound waves transmitted by the ultrasound device 320 are incident on a target region 322 with sufficient power and/or frequency (for instance, 50 kHz to about 5 MHz), for example, for treatment of diabetes (e.g., glucose homeostasis). The target region 322 may be any organ, organ system, organ region, and/or the like that may be targeted by the ultrasound device 320 for therapeutic treatment according to some embodiments. Non-limiting examples of the target region 322 may include the liver, the pancreas, the intestines, and/or any portion thereof. For instance, the target region 322 may be or may include the nerve plexus of the hepatic portal system of the liver.

In some embodiments, the ultrasound device 320 may include an ultrasonic head and a wireless power receiver. A wireless power transmitter 410 (e.g., a power source 330) may be used to provide wireless power signals to the receiver to power the ultrasound device 320 and/or to charge a battery or other electronic element configured to power the ultrasound device. In some embodiments, the wireless power transmitter 410 may be configured to provide RF signals, magnetic energy, electromagnetic energy, light energy, and/or the like.

In one embodiment, the power unit (e.g., power unit 322) of the ultrasound device 320 may be powered, at least in part, using a wired connection. For example, the power unit may include a wire configured to travel along the catheter 210 (and/or other PD tubing) to an external wired power source. In some embodiments, the wire may be configured to connect to a power source on the PD dialysis system 101 and/or to a different external, wired power source. In various embodiments, the wire may be embedded in the catheter 202, for instance, within an outside surface of the catheter 202 tubing.

In some embodiment, a patient sensor 440 may be configured to measure one or more patient physiological values. In one embodiment, the patient sensor 440 may be or may include a blood glucose unit or sensor that may be configured to measure the blood glucose of the patient. Other patient sensors may include devices for measuring blood pressure, temperature, fluid volume, and/or the like.

In some embodiments, the PD system 101 may correlate the blood glucose unit 440 with periodic glucose readings to determine efficacy and make recommendations to clinicians on the newfound ability for a patient to tolerate higher dextrose/lactose dialysate solution concentrations. A non-limiting example of a blood glucose unit 440 may include a continuous glucose monitor (CGM) worn by a patient. In some embodiments, the blood glucose readings may be provided to a control unit or application to automatically determine various PD parameters, such as the dialysate concentration (e.g., dextrose/lactose concentrations), dialysate volume, dwell time, PD cycles, and/or the like. For example, the PD system 101 may determine various PD parameters based on patient glucose levels, for instance, a glucose level (e.g., an average glucose level, a maximum glucose level, a minimum glucose level, and/or the like) of X may lead to a dialysate concentration of Y, or a dwell time of Z, etc. In various embodiments, the blood glucose readings may be read by a control unit or application to automatically determine various ultrasound therapy parameters, for instance, a glucose level of X may lead to an ultrasound frequency of Y, or a burst period of Z, etc.

Figure 5:
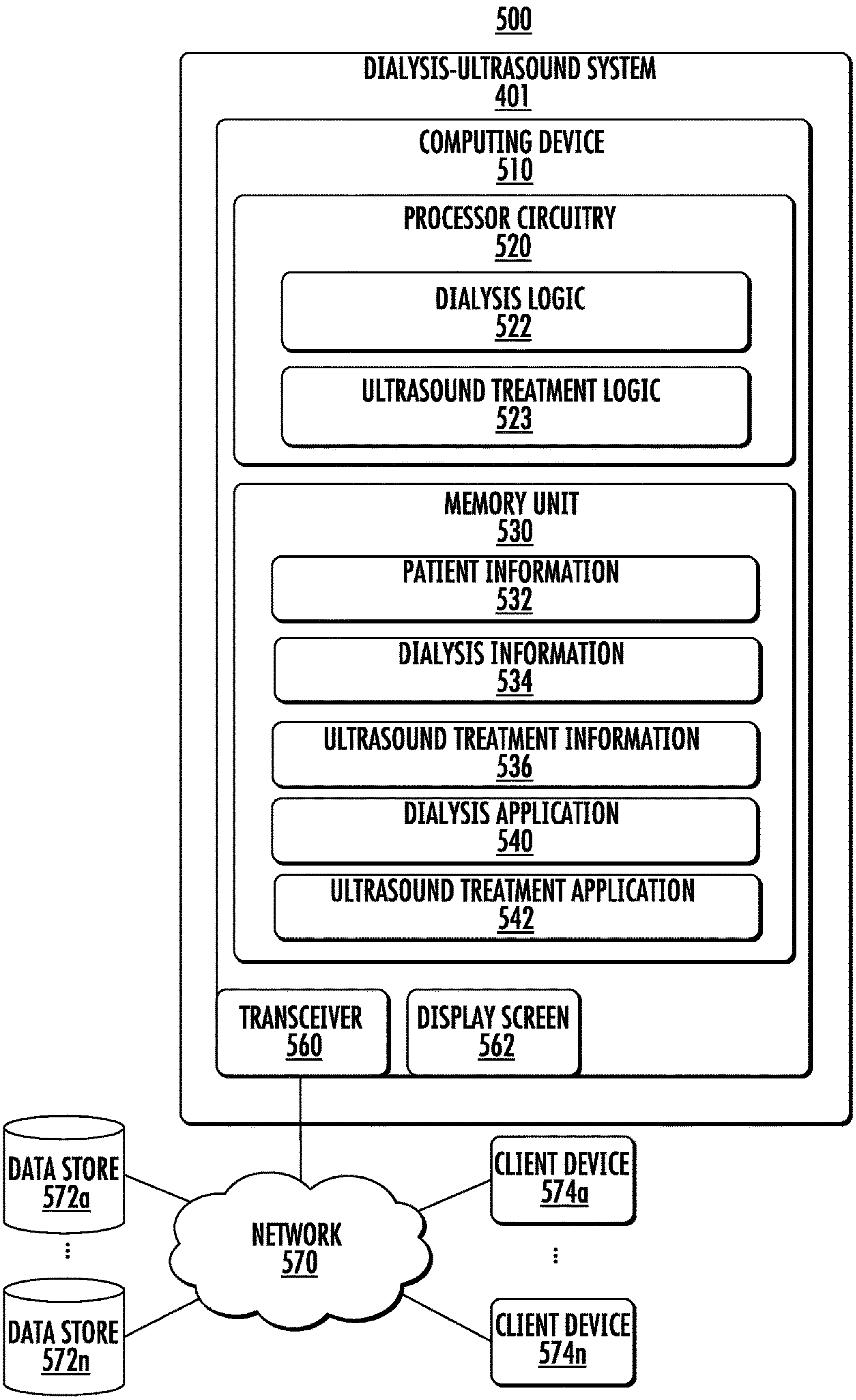
FIG. 5 illustrates a second exemplary operating environment in accordance with the present disclosure.

FIG. 5 illustrates a second exemplary operating environment in accordance with the present disclosure. As shown in FIG. 5, operating environment 500 may include a dialysis-ultrasound system 401. In various embodiments, the dialysis-ultrasound system 401 may include a computing device 510 communicatively coupled to network 570 via a transceiver 560.

In some embodiments, computing device 510 may be a server computer, PC, workstation or other type of computing device. In various embodiments, computing device 510 may be configured to control operational aspects of a PD system 101 and/or an ultrasound device and/or components thereof (e.g., ultrasound device 320, auxiliary units 321, control units 322, power units 323, power source 330, and/or the like). In some embodiments, computing device 510 may operate as a control unit (e.g., control unit 322) for an ultrasound device (e.g., ultrasound device 320 and/or a dialysis machine (e.g., dialysis machine 100).

For example, the computing device 510 may be arranged within the housing 106 of the dialysis machine 100 to provide user interface and/or control operations to the dialysis machine 100 and/or the ultrasound device 320 associated with the patient using the dialysis machine 100. For instance, the computing device 510 may provide the functionality for the touch screen 118 and the control panel 120. In another example, the computing device 510 may provide user interface and control operations for the ultrasound device 320. For example, the computing device 510 may include a display screen 562 (which may be or may include user interface 118) for providing input for controlling the ultrasound device 320 and/or components thereof (e.g., auxiliary units 321, control units 322, power units 323, power source 330, and/or the like). For example, a user can view, modify, and/or the like the ultrasound frequency, burst period, burst duration, and/or the like of the ultrasound device 320 using the computing device 510 via the display screen 562.

In various embodiments, the functions, operations, configurations, data storage functions, applications, logic, and/or the like described with respect to computing device 510 may be performed by and/or stored in one or more other computing devices (not shown), for example, coupled to the computing device 510 via a network 570 (for instance, one or more of client devices 574*a-n*). A single computing device 510 is depicted for illustrative purposes only to simplify the figure. Embodiments are not limited in this context.

The computing device 510 may include a processor circuitry 520 that may include and/or may access various logics, software, instructions, hardware, and/or the like for performing processes according to some embodiments. For instance, the processor circuitry 520 may include and/or may access a dialysis logic 522 and/or an ultrasound treatment logic 524. The processing circuitry 520, dialysis logic 522, ultrasound treatment logic 524, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, variations thereof, combinations of any of the foregoing, and/or the like. In some embodiments, for example, the dialysis logic 522 and/or the ultrasound treatment logic 524 may be or may include instructions being executed via the processor circuitry 520 (for instance, when executing a dialysis application 540 and/or an ultrasound treatment application 542).

Although the dialysis logic 522 and the ultrasound treatment logic 524 are depicted in FIG. 5 as being within the processor circuitry 520, embodiments are not so limited. For example, the dialysis logic 522, the ultrasound treatment logic 524, and/or any component thereof may be located within an accelerator, a processor core, an interface, an individual processor die, implemented entirely as a software application (for instance, the dialysis application 540 and/or the ultrasound treatment application 542) and/or the like.

Although the dialysis application 540 and the ultrasound treatment application 542 are depicted as separate applications, these applications may be the same application (e.g., a dialysis-ultrasound application), for instance, as modules and/or the like.

The memory unit 530 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 530 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

The memory unit 530 may store various types of information and/or applications for an a dialysis-ultrasound treatment process according to some embodiments. For example, memory unit 530 may store patient information 532, dialysis information 534, ultrasound treatment information 536, the dialysis treatment application 540, and/or the ultrasound treatment application 542. In some embodiments, some or all of the patient information 532, the dialysis information 534, the ultrasound treatment information 536, the dialysis treatment application 540, and/or the ultrasound treatment application 542 may be stored in one or more data stores 572*a-n* accessible to the computing device 510 via the network 570. For example, one or more of the data stores 572*a-n* may be or may include a health information system (HIS), an electronic medical (or health) record (EMR) system, a dialysis information system (DIS), a picture archiving and communication system (PACS), a Centers for Medicare and Medicaid Services (CMS) database, U.S. Renal Data System (USRDS), a proprietary database, and/or the like.

In some embodiments, the computing device 510 may be or may include a specifically programmed computing device configured for controlling a dialysis machine and/or an ultrasound device according to various embodiments. In various embodiments, the computing device 510 may be embedded or otherwise integral to a dialysis machine (for instance, within a housing 106 of the dialysis machine 100).

In various embodiments, the dialysis logic 522, for instance, via execution of the dialysis treatment application 540, may operate to control functional aspects of a dialysis machine to perform a dialysis process. For example, the dialysis logic 522 may operate to control the dialysis machine 100 to perform a PD process (e.g., controlling the fill and drain steps, monitoring for dwell time, forming the dialysate, and/or the like). In various embodiments, the ultrasound treatment logic 524, for instance, via execution of the ultrasound treatment application 542, may operate to control functional aspects of an ultrasound device to perform an ultrasound process. For example, the ultrasound treatment logic 524 may operate to control the ultrasound device 320 to perform an ultrasound treatment.

In some embodiments, the patient information 532 may include information, measurements, and/or historical information associated with a patient, including demographic information, health information (e.g., PD parameters, blood glucose levels, ultrasound parameters, and/or the like), physiological information, and/or the like. In various embodiments, the dialysis information 534 may include information associated with performing dialysis on a patient including, without limitation, PD parameters such as dialysate concentration, fill volume, dwell time, and/or the like. In exemplary embodiments, the ultrasound treatment information 536 may include information associated with performing ultrasound therapy on a patient, including the target region and ultrasound therapy parameters such as ultrasound frequency, burst period, burst duration, ultrasound treatment duration, and/or the like.

In various embodiments, the dialysis application 540 may include a software application configured to manage a dialysis treatment of a patient, for example, via control of a dialysis machine according to some embodiments. In exemplary embodiments, the ultrasound treatment application 542 may include a software application configured to manage an ultrasound treatment of a patient, for example, via control of an ultrasound device and/or components thereof according to some embodiments.

In various embodiments, the patient information 532, the dialysis information 534, and/or the ultrasound treatment information 536 may include one or more data structures, tables, databases, computational models (e.g., machine learning and/or artificial intelligence models) configured to control a dialysis process and/or an ultrasound treatment process based on one or more patient factors. A non-limiting example of a patient factor may include blood glucose information, for example, indicating a status of a patient's diabetic condition. Blood glucose information may include, but is not limited to, a current blood glucose reading, historical blood glucose readings, a blood glucose trend, a blood glucose maximum, a blood glucose minimum, an average blood glucose. Another non-limiting example of a patient factor may be a prescription (e.g., for insulin), indicating a severity of a patient's diabetic condition.

For example, a computational model or other data structure may be configured to receive blood glucose information of a patient to determine ultrasound therapy parameters. For instance, an ultrasound frequency, burst period, and/or burst duration may be determined based on the blood glucose level of the patient. In some embodiments, blood glucose values may be associated with an ultrasound frequency, burst period, and/or burst duration (e.g., greater signal intensity and/or burst duration/frequency for greater blood glucose levels). In various embodiments, the changes in the ultrasound therapy parameters may be automatically and/or dynamically changed based on the patient factors, such as blood glucose levels. For example, the ultrasound therapy application 542 may receive or determine the blood glucose level of a patient and control the ultrasound frequency based on the blood glucose level. In various embodiments, the dialysis process may be controlled based on the patient factors. For instance, the dialysis application 540 may receive or determine the blood glucose level of a patient and control one or more of the PD parameters (e.g., dialysate concentration) based on the blood glucose level.

In some embodiments, the computing device 510, for instance, via the dialysis application 540 and/or the ultrasound therapy application 542 may control the dialysis process and/or the ultrasound treatment process based on parameters, active process step, and/or the like of a treatment process. For example, ultrasound treatment via the ultrasound device 320 may be performed only during the PD dwell time/cycle and/or during a drain step. In another example, the dialysate concentration for the PD treatment may be determined based, at least in part, on one or more ultrasound parameters.

In some embodiments, the PD treatment and the ultrasound treatment may be performed, at least partially, concurrently. In various embodiments, the PD treatment and the ultrasound treatment may be performed individually at separate times.

In various embodiments, at least a portion of the information, software, hardware, and/or functionality associated with the ultrasound treatment process of computing device 510 may be stored within and/or performed by the control unit 322.

Included herein are one or more logic and/or process flows representative of exemplary methodologies for performing novel aspects of the disclosed embodiments. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic or process flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 6:
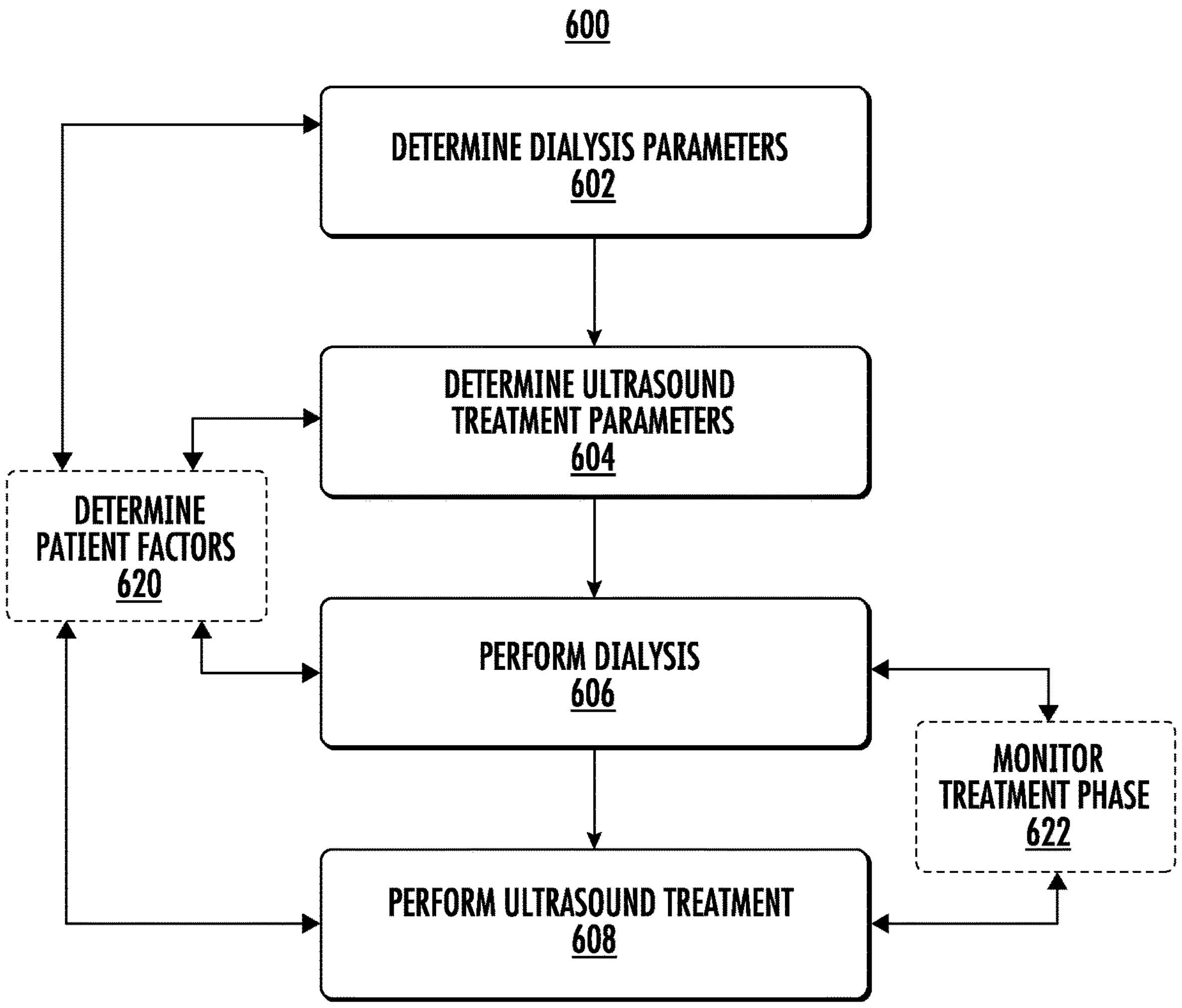
FIG. 6 illustrates a process flow in accordance with the present disclosure.

FIG. 6 illustrates an embodiment of a process or logic flow 600. Logic flow 600 may be representative of some or all of the operations executed by one or more embodiments described herein, such as the dialysis system 101 and/or the computing device 510. In some embodiments, logic flow 600 may be representative of some or all of the operations of a dialysis-ultrasound process according to some embodiments. In various embodiments, a dialysis-ultrasound process may include dialysis being performed, at least partially, concurrently with ultrasound treatment. In other embodiments, a dialysis-ultrasound process may include dialysis and ultrasound therapy being performed individually at separate times. Accordingly, the blocks or steps of logic flow 600 may not necessarily be performed in order and/or concurrently.

At block 602, the logic flow 600 may determine dialysis parameters. For example, dialysis information 534 may include information for performing dialysis, such as a dialysate concentration or formula, a dwell time, a drain time, number of cycles, and/or the like. At block 604, the logic flow 600 may determine ultrasound treatment parameters. For example, ultrasound treatment information 536 may include information for performing an ultrasound treatment, such as an ultrasound frequency (or frequency range), burst period, burst duration, and/or the like.

In various embodiments, one or more of the parameters determined at block 602 and/or 604 may be based on a prescription. In other embodiments, one or more of the parameters determined at block 602 and/or 604 may be based on patient factors. In some embodiments, the logic flow 600 may operate to determine or access patient factors 620. In various embodiments, patient factors may include current and/or historical patient measurements, including, without limitation, blood glucose levels, blood pressure, temperature, patient fluid volume, and/or the like. As indicated in FIG. 6, the determined patient factors 620 may be used to determine one or more of parameters at block 602 and/or block 604. In addition, in some embodiments, the determined patient factors 620 may be used to determine the performance of dialysis (block 606) and/or an ultrasound treatment (block 608). For example, the blood glucose level of a patient may cause a step of dialysis and/or an ultrasound treatment to be stopped, started, and/or modified.

At block 606, the logic flow 600 may perform dialysis. For example, the computing device 510 may control the dialysis machine 101 to perform a dialysis process on a patient using the PD parameters. At block 608, the logic flow 600 may perform an ultrasound treatment. For example, the computing device 510 may control the ultrasound device 320 to perform an ultrasound process on a patient using the ultrasound parameters. For example, the computing device 510 may control the target region (for instance, via targeting or focusing of the ultrasound waves), ultrasound frequency, burst period, and/or burst duration. During the ultrasound treatment, a therapeutically effective dose of ultrasound (e.g., pulsed focused ultrasound) may be provided to the target region. In some embodiments, the therapeutically effective does may be a dose sufficient to stimulate insulin production/secretion, facilitate or cause glucose homeostasis, and/or the like.

In some embodiments, the logic flow 600 may monitor the treatment phase of an active treatment (e.g., dialysis and/or ultrasound treatment) and may stop, start, and/or modify performance of one of the treatments. For example, the logic flow 600 may determine that the fill phase of a dialysis treatment has started (e.g., filling the patient with PD fluid) and may stop or modify an active ultrasound therapy. In another example, the logic flow 600 may prevent one treatment from being active during another treatment. For instance, the logic flow may determine that the PD cycle for a patient is set to start at certain time and may prevent ultrasound treatment during the duration of the PD cycle and/or treatment.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A system, comprising:

a peritoneal dialysis (PD) catheter configured to be implanted in the peritoneal cavity of a patient for PD treatment, wherein a distal end of the PD catheter includes a plurality of holes and is configured to be positioned in a base of the peritoneal cavity of the patient when the PD catheter is in an implanted position such that dialysate solution can flow in and out of the peritoneal cavity via the plurality of holes; and an ultrasound device configured to emit ultrasound waves, the ultrasound device connected to the PD catheter such that, when the PD catheter is in the implanted position, the ultrasound device is disposed within the peritoneal cavity of the patient and spaced apart from the distal end of the PD catheter such that the ultrasound device is configured to provide ultrasound therapy to a liver of the patient.

2. The system of claim 1, the ultrasound device comprising one of a high-intensity focused ultrasound (HIFU) device or peripheral focused ultrasound stimulation (pFUS) device.

3. The system of claim 1, wherein the ultrasound device is arranged to provide ultrasound energy to a nerve plexus of a hepatic portal system of the liver.

4. The system of claim 1, the ultrasound device comprising a power unit configured to be wirelessly charged via a wireless power source.

5. The system of claim 4, the power unit operative via electrodynamic wireless power transfer (EWPT).

6. The system of claim 4, the power unit operative via one or more of a triboelectric effect, photonic power transfer, or kinetic charging.

7. The system of claim 1, further comprising:

a patient sensor configured to measure a patient factor; and a dialysis machine fluidically coupled to the PD catheter and configured to perform PD on the patient, at least one PD parameter of the PD determined based on the patient factor.

8. The system of claim 7, the patient sensor comprising a blood glucose sensor.

9. The system of claim 7, the PD parameter comprising a dialysate concentration.

10. The system of claim 1, the ultrasound therapy configured to treat diabetes;

wherein the ultrasound device includes one or more auxiliary devices selected from an amplifier, a radio frequency (RF) amplifier, or an impedance matching network; and wherein the pressure sensor is integrated with or coupled with the PD catheter or the ultrasound device.

11. A method, comprising:

implanting a peritoneal dialysis (PD) catheter into an implanted position in the peritoneal cavity of a patient such that a distal end of the PD catheter is positioned in a base of the peritoneal cavity, wherein the PD catheter includes an ultrasound device configured to emit ultrasound waves within the peritoneal cavity, the ultrasound device being spaced apart from the distal end of the PD catheter in a position within the peritoneal cavity to provide ultrasound therapy to a liver of the patient when implanted in the peritoneal cavity;

performing PD treatment on the patient by flowing dialysate in and out of the peritoneal cavity via the distal end of the PD catheter when the PD catheter is in the implanted position; and performing ultrasound therapy on the liver by causing the ultrasound device to emit the ultrasound waves incident on the liver when the PD catheter is in the implanted position.

12. The method of claim 11, the ultrasound device comprising one of a high-intensity focused ultrasound (HIFU) device or peripheral focused ultrasound stimulation (pFUS) device.

13. The method of claim 12, wherein the ultrasound device is arranged to provide ultrasound energy to a nerve plexus of a hepatic portal system of the liver.

14. The method of claim 13, the ultrasound device comprising a power unit configured to be wirelessly charged via a wireless power source.

15. The method of claim 14, the power unit operative via electrodynamic wireless power transfer (EWPT).

16. The method of claim 14, the power unit operative via one or more of a triboelectric effect, photonic power transfer, or kinetic charging.

17. The method of claim 11, further comprising:

receiving a measurement of a patient factor determined via a patient sensor;

performing PD on the patient using at least one PD parameter determined based on the patient factor.

18. The method of claim 17, the patient sensor comprising a blood glucose sensor.

19. The method of claim 17, the PD parameter comprising a dialysate concentration.

20. The method of claim 11, the ultrasound therapy configured to treat diabetes;

wherein the ultrasound device includes one or more auxiliary devices selected from an amplifier, a radio frequency (RF) amplifier, or an impedance matching network; and wherein the pressure sensor is integrated with or coupled with the PD catheter or the ultrasound device.

* * * * *